United States Patent [19]

Ng

[11] Patent Number: 5,820,623

[45] Date of Patent: Oct. 13, 1998

[54] ARTICULATED ARM FOR MEDICAL PROCEDURES

[76] Inventor: Wan Sing Ng, Blk 827, Jurong West Street 81, #06-278, Singapore 640827, Singapore

[21] Appl. No.: 793,183

[22] PCT Filed: Jun. 20, 1995

[86] PCT No.: PCT/SG95/00009

§ 371 Date: May 5, 1997

§ 102(e) Date: May 5, 1997

[87] PCT Pub. No.: WO97/00649

PCT Pub. Date: Jan. 9, 1997

[51] Int. Cl.[6] ................................................. A61B 17/00
[52] U.S. Cl. .................... 606/1; 606/130; 318/568.11; 318/568.21
[58] Field of Search ................ 606/1, 130; 433/51; 318/568.11, 568.21

[56] References Cited

U.S. PATENT DOCUMENTS

| | | | |
|---|---|---|---|
| 4,638,798 | 1/1987 | Shelden et al. | 128/303 |
| 4,941,826 | 7/1990 | Loran et al. | 433/51 |
| 5,080,662 | 1/1992 | Paul | 606/130 |
| 5,279,309 | 1/1994 | Taylor et al. | 128/782 |

FOREIGN PATENT DOCUMENTS

| | | |
|---|---|---|
| 0416863 | 9/1990 | European Pat. Off. . |
| 869842 | 3/1953 | Germany . |
| 9317620 | 9/1993 | WIPO . |

*Primary Examiner*—Michael Powell Buiz
*Assistant Examiner*—Julian W. Woo
*Attorney, Agent, or Firm*—George O. Saile; Stephen B. Ackerman

[57] ABSTRACT

An articulated arm is disclosed which can be used to firmly support and position a variety of medical tools, including surgical or diagnostic instruments flexibly in space. Though some of its sub-assemblies may be computer controlled, thus autonomous in accordance to some pre-programmed sequence, manual control is also possible. When its sub-assemblies are suitably controlled using computer software, and with a suitable cutting instrument, the arm is capable of generating a barrel shape cavity or, for that matter, any desired shape of cavity (or treatment volume) that is within the work envelope of the arm. The ideal position of the focal point is dynamically variable as required, either with respect to the tool or the absolute frame of reference, during an intervention. A suitable type of intervention is minimally invasive surgery (MIS). Apart from cutting (or resection), the articulated arm, by virtue of its robotic nature, can also be used to perform such tasks as biopsies and radiation seed implantation, where positional accuracy and repeatability are highly desirable. The articulated arm is a universal computer assisted holder for a wide range of medical tools, in particular endoscopes for treatment of urological disorders.

19 Claims, 13 Drawing Sheets

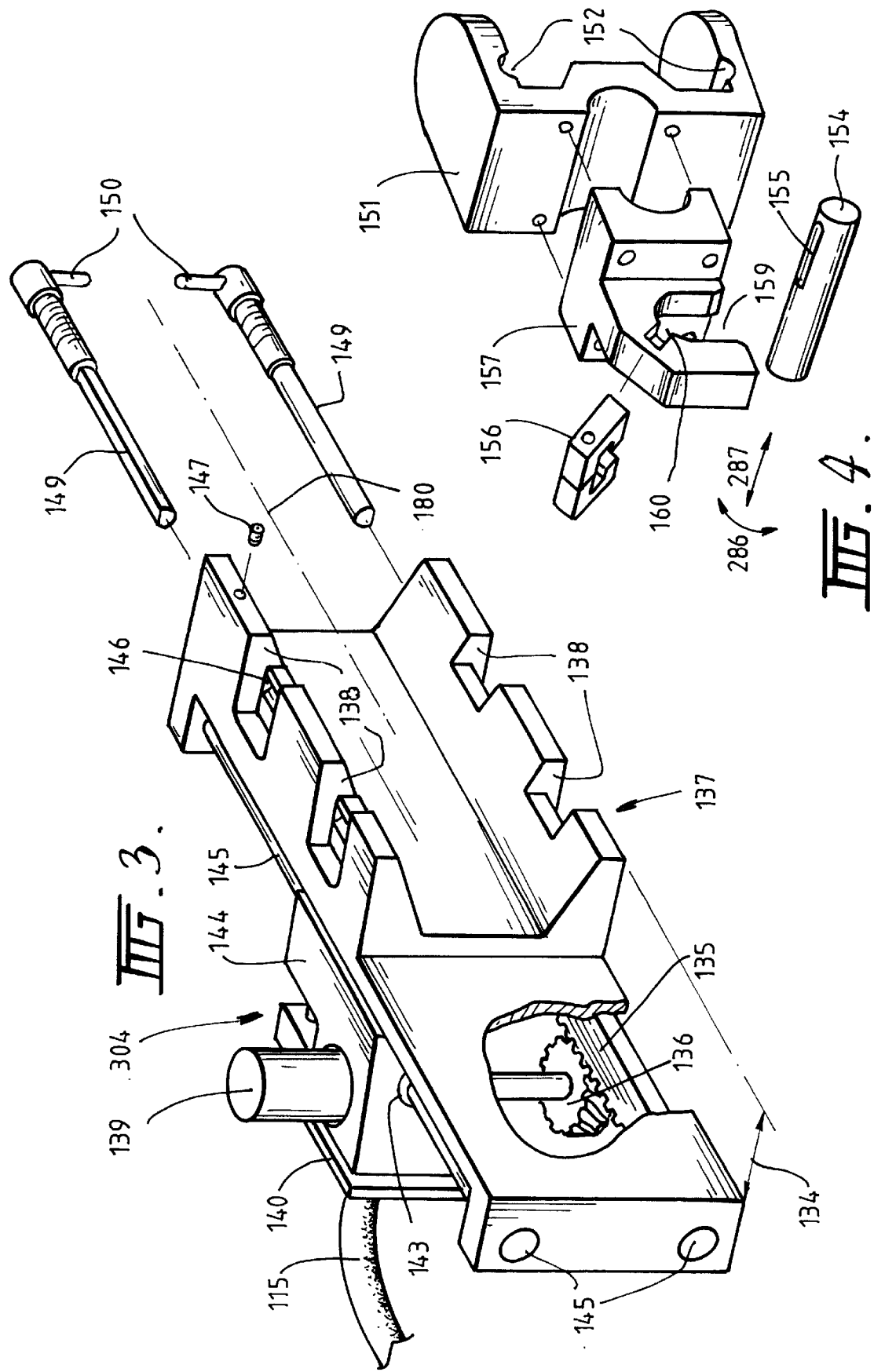

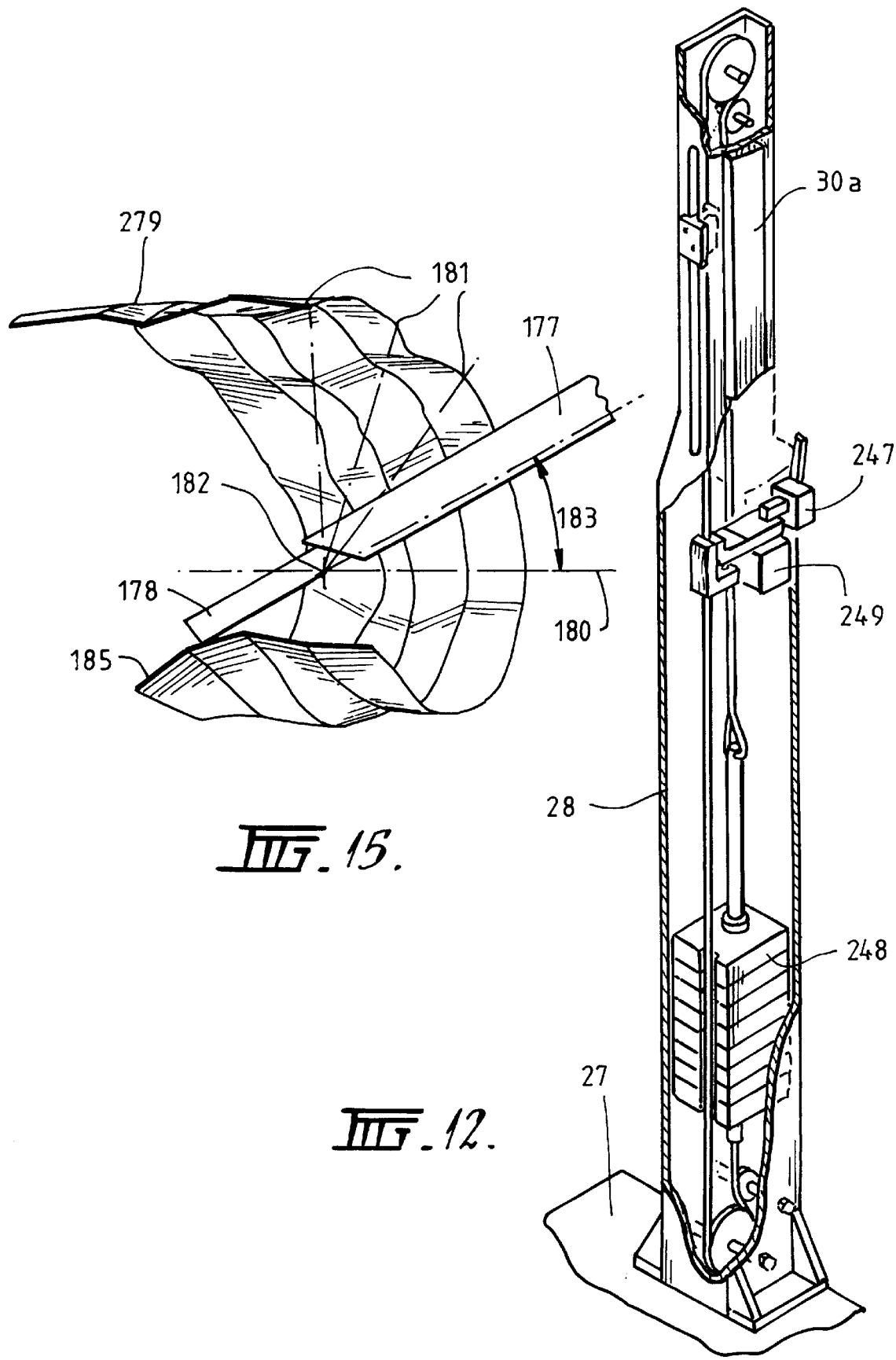

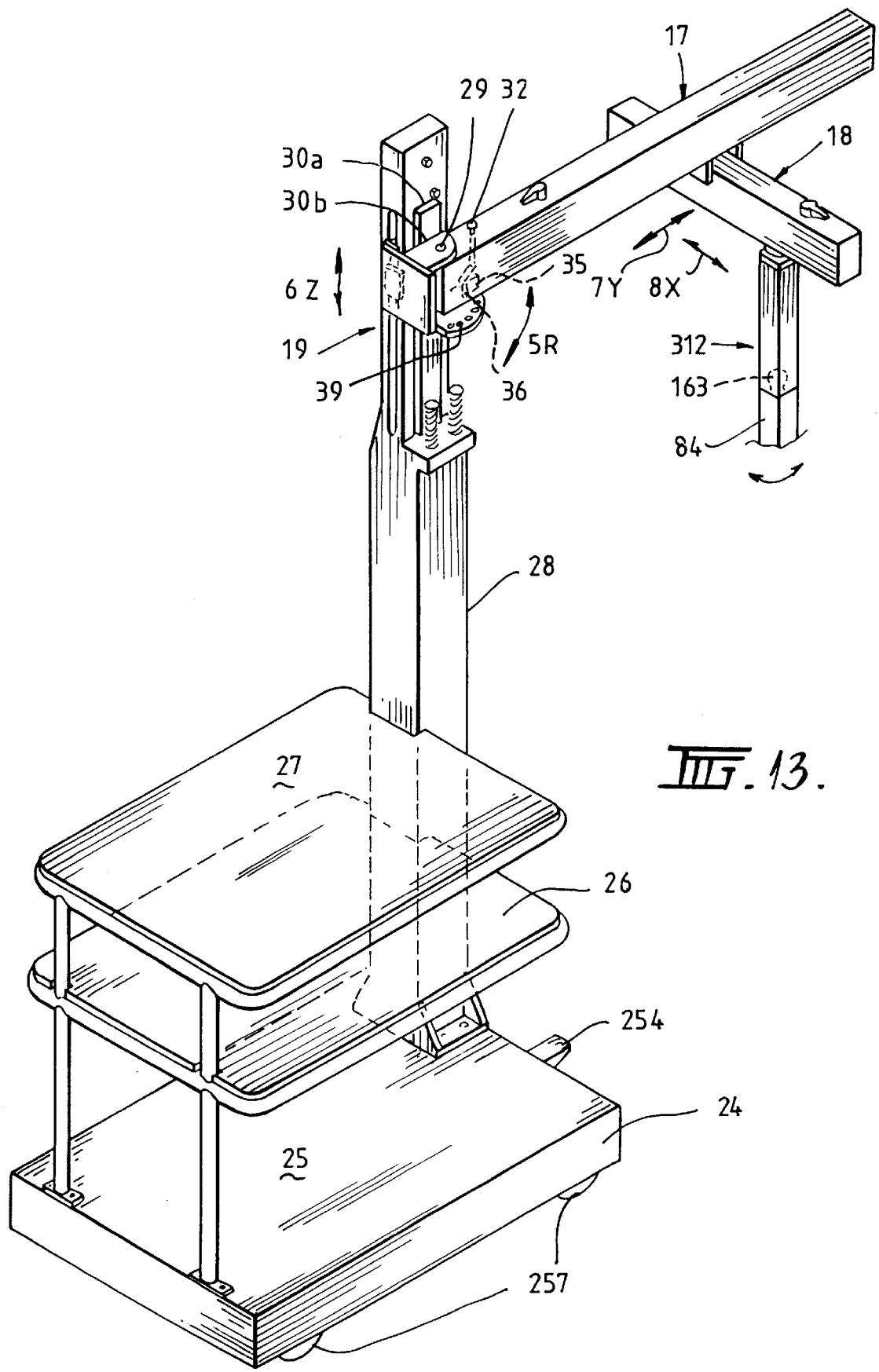

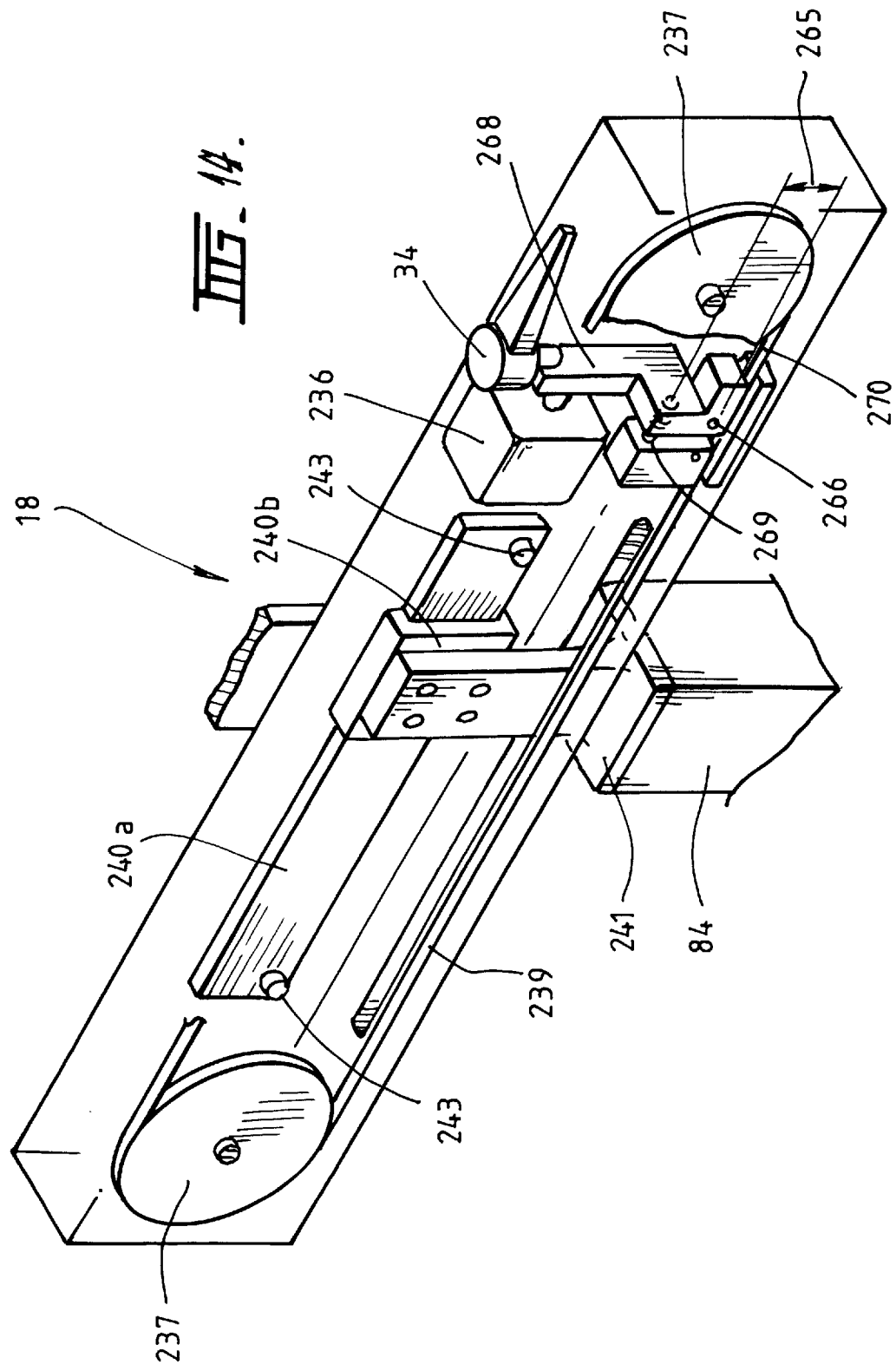

ARTICULATED ARM FOR MEDICAL PROCEDURES

FIELD OF THE INVENTION

This invention relates to an articulated arm for conducting medical procedures and relates particularly, though not exclusively, to a robotic system which is suitable for use in medical applications, whether it be surgical, therapeutic or diagnostic. The articulated arm may be used to provide a firm support for a range of surgical or diagnostic tools.

BACKGROUND TO THE INVENTION

Computerised machines and robotic technology have been used very successfully in many industries, especially where repetitive (hence laborious), accurate or hazardous tasks are to be handled with speed. The positional repeatability, certainty, accuracy and precision of a robot has recently found application in positioning surgical tools in the operating theatre. In particular, minimally invasive procedures have great potential to exploit robotic technology.

It is known in the art that non-invasive surgeries, such as ESWL (extracorporeal shockwave lithrotripsy) and high intensity ultrasound, for the fragmentation of kidney stones, or otherwise, have employed computer assisted positioning systems to place the target, which is in the patient, in line with the firing line of the treatment tool which is outside the patient.

However, most minimally invasive surgery (MIS) procedures require the use of a tool or a number of macroscopic scale tools called endoscopes, which can be rigid or flexible, enter through small natural, or incised, openings on the patient, to treat the diseased portions of an organ internal to the body. Endoscopes for MIS procedures usually carry optic fibres for the delivery of cool light for viewing the operating site. Such views can be seen through an eyepiece, or shown on a TV monitor (called video surgery), for comfortable and enlarged viewing. These views (direct endoscopic vision), however, only provide sight on the immediate operating environment. The surgeon does not have a clear idea of what lies outside this view. It often requires his/her skills and experience to identify his/her whereabouts in the patient when new tissues unfold as a result of cutting, which can be dangerous.

Modern medical imaging modalities, such as computer tomography (CT), magnetic resonance imaging (MRI) and ultrasound (US) offer the possibility of a computer-assisted three-dimensional view, by displaying on a flat monitor a 3D image of the organ under treatment or observation. This image is capable of being superimposed onto the patient as seen through a pair of specially prepared goggles, to guide the surgeon during an MIS. In this manner, the time consumed in resection and suturing can be cut down by a clear view of the operating site. 3D data, composed by the computer can also be used directly, in addition to display, by suitable supervisory or control software of a motion control system, to control the movement of the cutter/endoscope carried by a robot of suitable configuration. This way, the surgeon and the computing system know what is beyond the immediate operating environment.

Examples of active robotic intervention in MIS procedures are numerous, including TURP (transurethral resection of the prostate), automated colonoscopy, stapedectomy, and ENT (ear-nose-throat) procedures. An example of an open procedure that has been demonstrated with robotic intervention is cementless hip bone implant/replacement, where a precise cavity to fit a pre-selected implant is milled both locationally and dimensionally accurately in the femur by an industrial robot that carries the milling cutter.

EP 0,416,863 (WICKHAM) describes a frame for positioning and guiding a medical implement such as a resectoscope, which can be used for the non-invasive surgical treatment of the prostate. The frame comprises an annular frame member (10,50) and an annular ring (15,57) held captive and rotatable about its axis in a plane parallel to that of the frame member. An arcuate bow (18,65) extends across the ring and carries a mounting block (20,66) for the implement, the movement of which is controlled by moving the block along the bow and by moving the ring relative to the frame member. The radius of the ring, the radius of curvature of the bow and the distance of the tip of the medical implement from the bow are selected such that movement of the implement around the ring and across the bow will sweep out two substantially conical regions on the side of the ring remote from the bow. In the case where the medical implement is a resectoscope, the smaller conical region is that of the material to be removed to leave a conical orifice in the prostate. One form of the frame may be mounted to a table by means of a clamp, whilst another form of the frame may be secured to an overhead mounting. Motor drives may be provided for rotating the annular ring, traversing an implement mounted across the bow and for operating the implement.

The frame of EP 0,416,863 is not readily modified to perform operations other than TURP or other cutting modalities for TURP than electrocauterisation. In particular, the mounting block (20,66) is not easily adapted to carry other types of medical tool and the annular ring (15,57) also places a constraint on the type of medical tool that can be mounted on the frame because of the limited area for movement of the tool within the circumference of the annular ring. Also, the frame of EP 0,416,863 must be mounted on or in connection with the operating table which further restricts the ease with which it can be used or modified for performing other medical procedures. Set up of the frame in the operating theatre is extremely difficult. An assistant is needed to manually carry the entire frame (weighing about 8 kg), confined to the ball joints of the mounting frame, to engage the mounting block (20,66) with a bracket on the resectoscope. The assistant has to manually lock two ball joints when engagement is accomplished. The assistant's presence can cause problems and obstruction to the sterilised area. Also the frame does not allow for quick emergency manual takeover. With the motorised version, wires cannot be properly harnessed, due to the frame design, and therefore cause obstruction and are a safety hazard. Complete sterility of the frame cannot be achieved.

The present invention was developed with a view to providing an articulated arm which can be readily adapted to carry a wide range of medical tools for performing various medical procedures.

SUMMARY OF THE INVENTION

According to the present invention there is provided an articulated arm for performing medical procedures with a medical tool, the arm comprising:

an arcuate member slidably mounted on a first movable support member;

a tool holder for holding the medical tool in an operational position, said tool holder being carried by the arcuate member; and, a first drive assembly provided on said first support member for slidably moving said arcuate member with said tool holder, wherein said tool holder can be moved along an arcuate path so as to alter the operational position of the tool in a predetermined manner.

Preferably the articulated arm further comprises a second drive assembly provided in connection with said tool holder for moving said tool holder along a linear path, said linear path intersecting an axis passing through the centre of curvature of said arcuate path. The arcuate member may be removably mounted on said first support member, and wherein another arcuate member having a different radius of curvature can be slidably mounted on the first support member if desired.

Preferably the articulated arm further comprises a third drive assembly mechanically coupled to said first support member for pivoting said first support member about a first drive axis, whereby said tool holder carried by the arcuate member can also be pivoted about said first drive axis.

Advantageously said first support member is coupled to said third drive assembly by means of a coupling adapted to produce an offset between said first drive axis and a longitudinal axis of said first support member whereby, in use, a central axis of the medical tool held in the tool holder intersects said first drive axis so as to define a pivot point of the tool.

Preferably said coupling is a removable coupling which can be replaced with a different coupling to produce a different offset so as to accommodate a different medical tool.

Preferably the articulated arm further comprises a second support member for supporting said third drive assembly, said second support member being provided with a fourth drive assembly for moving said third drive assembly in a linear direction whereby, in use, said tool holder together with the arcuate member can also be moved in said linear direction.

The following description will be given with particular reference to the use of the articulated arm in a procedure commonly known as TURP (transurethral resection of the prostate), which has been regarded as the gold standard in treating Benign Prostate Hyperplasia (BPH). The cutting modality assumed is the electrocauterisation technique. The medical tools employed in TURP are urological endoscopes, in particular, a resectoscope which comprises a telescopic lens, an electrode, an outer sheath and a working element equipped with a spring loaded handle of standard configuration. It is to be understood that the articulated arm can be used equally successfully in many other medical procedures, and is not limited in its application to TURP. Furthermore, the articulated arm is capable of holding a wide variety of other medical tools and is not restricted to urological endoscopes.

BRIEF DESCRIPTION OF THE DRAWINGS

In order to enable the current invention to be more readily understood, reference will now be made to the accompanying figures which illustrate, by way of example only, an embodiment of the articulated arm, and in which:

FIG. 3 illustrates a preferred pivot length drive sub-assembly of the articulated arm, including a preferred tool holder;

FIG. 4 illustrates a C-bracket sub-assembly employed with the tool holder of FIG. 3;

FIG. 12 shows a main column assembly including a pulley system and balancing weights;

FIG. 13 depicts a counterbalance support structure used with the articulated arm;

FIG. 14 illustrates a continuously lockable cable system used in the X, Y and Z arms of the counterbalance support system;

FIG. 15 shows schematically the tracing of a barrel shape contour beyond a focal point by a resectoscope held by the articulated arm;

DETAILED DESCRIPTION OF PREFERRED EMBODIMENTS

Figure 1:
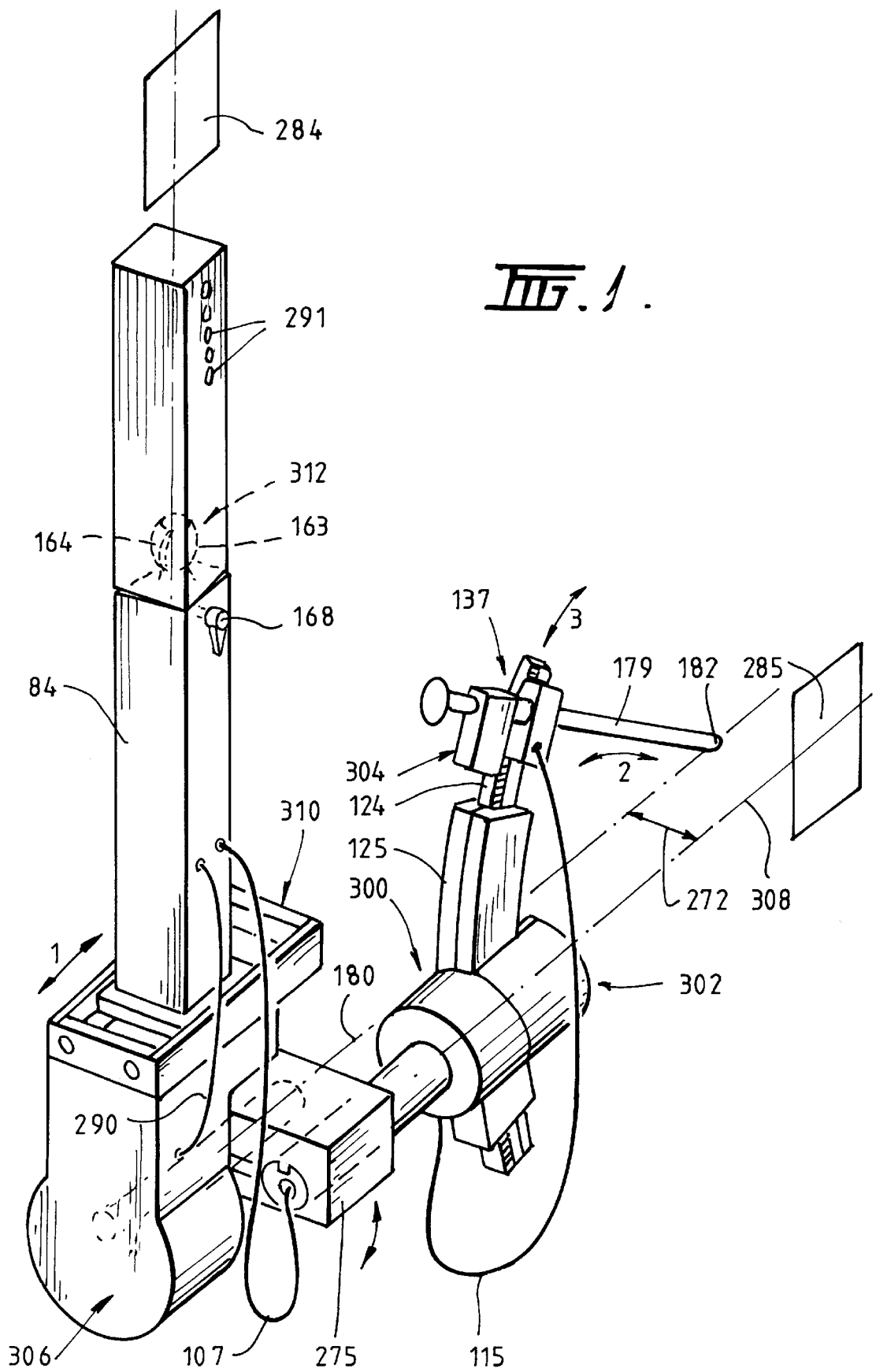
FIG. 1 is an isometric view of the articulated arm showing its various subassemblies.

A preferred embodiment of the articulated arm according to the invention is illustrated in FIG. 1. The arm comprises an arcuate member in the form of an arch 124 (see FIG. 7) slidably mounted on a first movable support member in the form of an arch support 300. A tool holder in the form of a carriage 137 (see FIG. 3), for holding a medical tool in an operational position, is carried by the arch 124. A first drive assembly in the form of arch drive assembly 302 (see FIG. 8) is provided on said arch support 300 for slidably moving the arch 124 with said carriage 137 so that the carriage can be moved along an arcuate path so as to alter the operational position of the tool in a predetermined manner. A second drive assembly in the form of a pivot length drive assembly 304 is provided in connection with the carriage 137 for moving the carriage along a linear path. Advantageously, the linear path along which the carriage 137 can move intersects with the centre of curvature of the arch 124.

The arch drive support 300 of the articulated arm is in turn carried by a second movable support member in the form of a vertical support column 84 by means of a coupling 275. The support column 84 is provided with a third drive assembly in the form of a ring drive assembly 306 in connection therewith, for pivoting the coupling 275 about a ring drive axis 180. The coupling 275 creates an offset 272 between a longitudinal axis 308 of the arch support 300 and the axis of rotation 180 of the ring drive assembly 306. The ring drive assembly 306 is in turn mounted in connection with a fourth drive assembly in the form of a head travel drive assembly 310 (see FIG. 11) provided at the base of support column 84. The head travel drive assembly is adapted to move the ring drive assembly 306 and all of the previously mentioned drive assemblies together with the arch support 300 and arch 124 along a linear path in a generally horizontal direction.

The articulated arm of the preferred embodiment provides freedom of motion in four independent directions. They are namely the head travel direction 1, the pivot length direction 2, the arch movement direction 3, and the ring rotation 4. The articulated arm typically has a pivot point 182 (FIGS. 1 and 15), which is the centre of curvature of the arch 124 of the arch drive assembly 302. The pivot point, through which a central axis of the tool carried by the arm preferably passes, advantageously lies on the ring rotational axis 180. This is achieved by having the arch displaced at an offset 272 from the arch drive assembly 302. Surgical or diagnostic tools can be attached onto the articulated arm via the carriage 137, (FIG. 3). It is usually desirable that the central, or desired, axis of these tools can be arranged to pass through the pivot point at all times and all configurations. This way, the tool axis forms the radial axis of the arch. Though the pivot point is fixed with respect to the arch 124, its position with respect to the tool body is variable. This is desirable in optimising the cutting strategy to be described later.

The pivot length drive assembly 304 (FIG. 3) is the nearest to the patient. It consists of the carriage 137, motor housing 144, a servo motor 139, a printed circuit board 140, guide rails 145, ball bushings 143, locking levers 150, a pair of set screws 147, and a rack 135 and pinion 136.

The carriage is shaped in such a way that clearances/offsets 134 are provided to clear the penis head and the resectoscope body. The centre line, which is also the central axis of the resectoscope, is arranged to align with the ring rotational axis 180.

The carriage 137 is supported on the guide rails 145 using ball bushings 143 housed in the motor housing. As is clearly illustrated in FIG. 3, the servo motor 139 is partly enclosed in its housing, with its shaft protruding underneath. The rack and pinion arrangement 135, 136 allows the motor 139 to drive the carriage and move it back and forth. The motor housing 144 remains stationary and is secured firmly by means of slot 142 onto an ear 299 milled on the arch 124, via three screws 298 (see FIG. 7). Any movement of the arch will carry the entire pivot length drive assembly 304 with it.

The printed circuit board 140 houses a differential line driver for the encoder signals to make them less susceptible to noise. The board is properly shielded to suppress electromagnetic interference (notably from a electrocauterisation unit commonly used in the operating theatre), and is mounted beside the motor housing 144. this board allows easy replacement of the motor, by providing electrical connectors on board.

The carriage 137 has two, or more, pairs of grooves 138 cut in a manner shown in FIG. 3. A selected pair of these grooves can be used to engage a C-bracket 151. The choice of groove depends on the desired location of the pivot point 182 with respect to a resectoscope body 179. The C-bracket 151 (see FIG. 4) is secured semi-permanently, using screws, onto a suitable portion of the resectoscope 179 and is sterilised together with the resectoscope. The C-bracket 151 forms one part of a bracket assembly, with another bracket 157. With a slight gap between the two parts of the bracket assembly, a sufficiently firm grip can be obtained when they are assembled onto a cylindrical portion of a tool such as an endoscope. Other forms of brackets may be readily made to fix onto other tools whose bodies are not cylindrical.

A protruding section on the bracket 157, as shown in FIG. 4, has a slot 159 through which a spindle 154, of corresponding diameter can pass. Recesses 160 are made on both sides of the thickness of the protruding section. A set of locking keys 156, constituting two halves, can be pushed manually, or under spring action, toward the slot 159 or away from it (see FIG. 4). The spindle 154 already mounted on the tip of a retractor (for example, a Greenberg retractor), is slid into the slot 159 of the protruding section. The entrance of the slot is slightly chamfered to ease entry. The spindle 154 is provided with a keyway 155. The spindle, or the C-bracket, can be rotated so that the keyway is directly in the path of the locking keys 156. Once aligned, the locking keys are pushed (manually) down to engage with the keyway 155 milled on the spindle, or, the spring action pushes the locking keys 156 into the keyway 155. This removes two degrees of freedom, 286 and 287 (see FIG. 4), so that there is no relative movement between the endoscope and the tool holder. Hence the endoscope can only be manipulated in ways permitted by the holder. To remove the endoscope is achieved simply by lifting the locking keys 156 upward so that they are not in the keyway 155. The spindle, and the holder it attaches onto, can now be removed from the protruding section; and detached from the endoscope.

Semi-circular grooves 152 cut on the C-bracket 151 are for the purpose of locking the bracket assembly when the C-bracket is engaged into grooves 138 cut on the carriage 137. The locking levers 150 have a flat 149 milled over a suitable length of its body. The levers are inserted into drilled holes 146 whose centres are offset so that the levers can be rotated to a position where the flat is flush with the grooves 138. When flush, the C-bracket can be inserted. The locking levers are prevented from dropping out by the set screws 147. Once the C-bracket is in place, the locking levers are turned 90 degrees or more so that the rounded portion of the levers now fill the grooves 152 cut on the C-bracket, thus locking it to the carriage 137.

Figure 8:
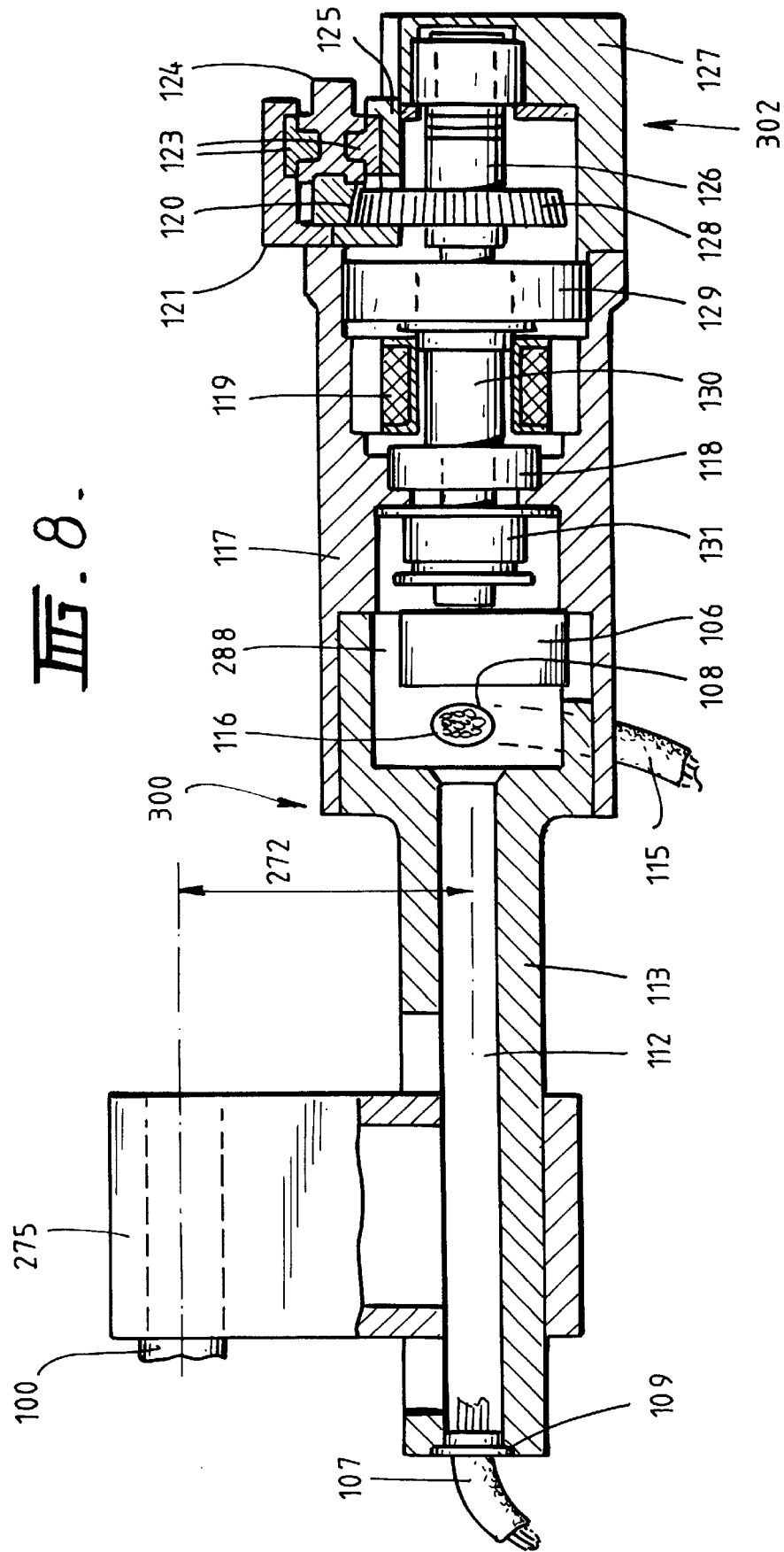
FIG. 8 is a section view through an arch drive sub-assembly of the articulated arm.

One embodiment of an arch drive assembly is illustrated in FIG. 8. As can be seen in FIG. 8, the arch drive consists of a drive shaft 130, bearing supports 118 and 129, a differential optical encoder 106 (or other form of position sensor), an electromagnetic brake 131 (preferably of normally locked type), bearing housing 117 and extension 113, and a servo motor 119. The bearing housing 117 and extension 113 together form the arch support 300. Axial grooves (not shown in FIG. 8) are cut on the annular surface of the housing 117 for the passage of wires. These wires, from the arch drive motor 119, encoder 106, brake 131, and from the arch 124 itself (limit switches or other additions), are collected at the recess where another branch of wires, (from the pivot length drive), terminate via an electrical connector 108. The wires 116 leading to the pivot length drive are bundled in a highly flexible insulated conduit 115, and with extra overhang to allow movement of the arch 124.

Wires collected within a recess 288 are all arranged to pass through a central hole 112 in the housing extension 113 at the end of which is another electrical connector 109. The use of connectors, as described above, is to facilitate changing of the coupling 275 to accommodate different diameter offsets 272 and tool lengths. From the end of the housing extension 113 (FIGS. 7 and 8), another flexible insulated and shielded conduit 107, with overhang to allow for ring rotation, bundles the wires and leads them to the vertical column 84 (FIG. 4) where it enters with a stress relief.

Figure 7:
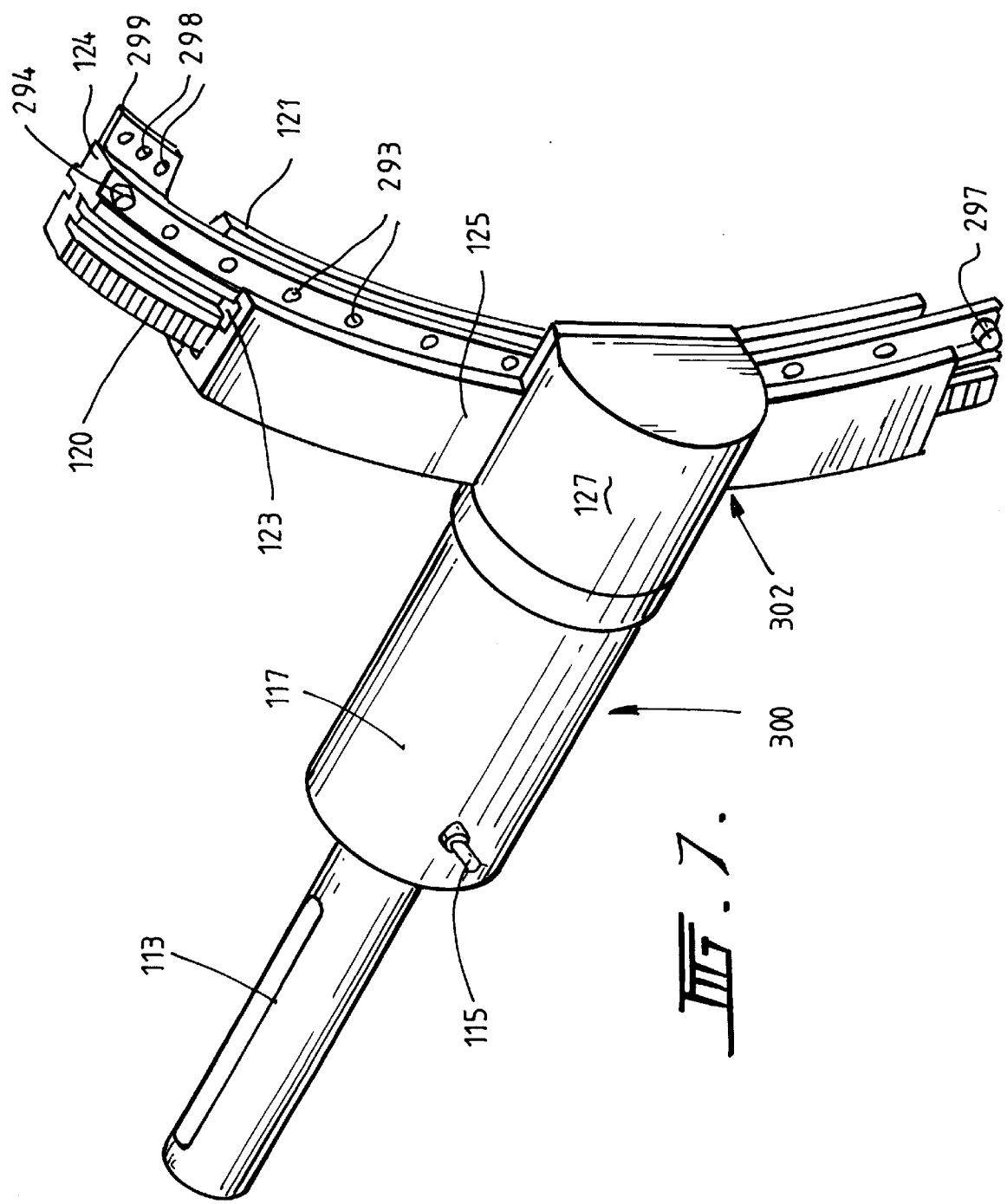
FIG. 7 is a perspective view of the arch drive sub-assembly of the articulated arm.

The arch drive assembly 302 carries and drives the arch 124 in the arch assembly (see FIGS. 7 and 8). The arch assembly consists of the arch 124 which has an external gear profile 120 cut on its circumference and is in the shape of an arc of a circle (of suitable radius and subtended angle), stiffeners 121 and 125, a cross shaft 126, a bevel gear set 128, a stopper 297, bearings 123, bearing tensioning screws 301, limit switches 294 (inside the stiffener 125, not visible), and a bearing housing 127. As mentioned before, the arch 124 has an ear 299 for the mounting of the pivot length drive assembly. When the arch drive motor 119 rotates the drive shaft 130, the motion is transmitted via the bevel gear set, 128 and 120, to the arch 124. The tool, mounted on the carriage 137 of the pivot length drive assembly, is caused to move along an arcuate path and the pivot point, formed by the centre of curvature of the arch, is at a suitable location along the tool body. This location can be adjusted either by moving the carriage 137 using the pivot length drive or by placing the tool with the C-bracket manually onto another available pair of grooves 138 on the carriage.

In the manual option, one can select the right pair of grooves 138 on the carriage, which can be one of several pairs limited by the length of the carriage, to engage the C-bracket. The other option is motorised and computerised, in that the pivot length drive can move the tool it carries with respect to the arch and hence its centre. Furthermore, the absolute position of the pivot point in space can be adjusted by moving the head travel drive assembly 310 after the articulated arm is locked onto the counterbalance support system.

The stiffeners 121, 125 act to strengthen the arch support and to give bearing surfaces for the smooth sliding movement of the arch 124. The arch has a series of holes 293 and 294 cut on its body at specific radial distances or intervals. The holes 293 allow the screwing on of a hard stop to positively prevent the arch 124 from overrun. Two hard stops are preferably provided to limit the arch travel in both directions. One stop is fixed, the placement of the other into the holes is dependent on the size of the target and is recommended by the software. The total arch travel is therefore adjustable. If a larger travel is needed, an arcuate member of larger subtended angle and/or having a different radius of curvature can be used. Indeed, the arcuate member may have a radius of curvature from anywhere between 5 cm to infinite (in the latter case the arcuate member is substantially straight so that the tool holder will be movable along a linear path). The optimum travel for treating the prostate, using electro-TURP is zero to 40 degrees with a radius of curvature of 250 to 300 mm.

An alternative means of accommodating different radii, rather than using an arcuate member having a different radius of curvature, is to use a tool holder or carriage 137 that has extended length to provide more slots 138. Each of these slots carries the tool at a different radius of curvature.

Figure 9:
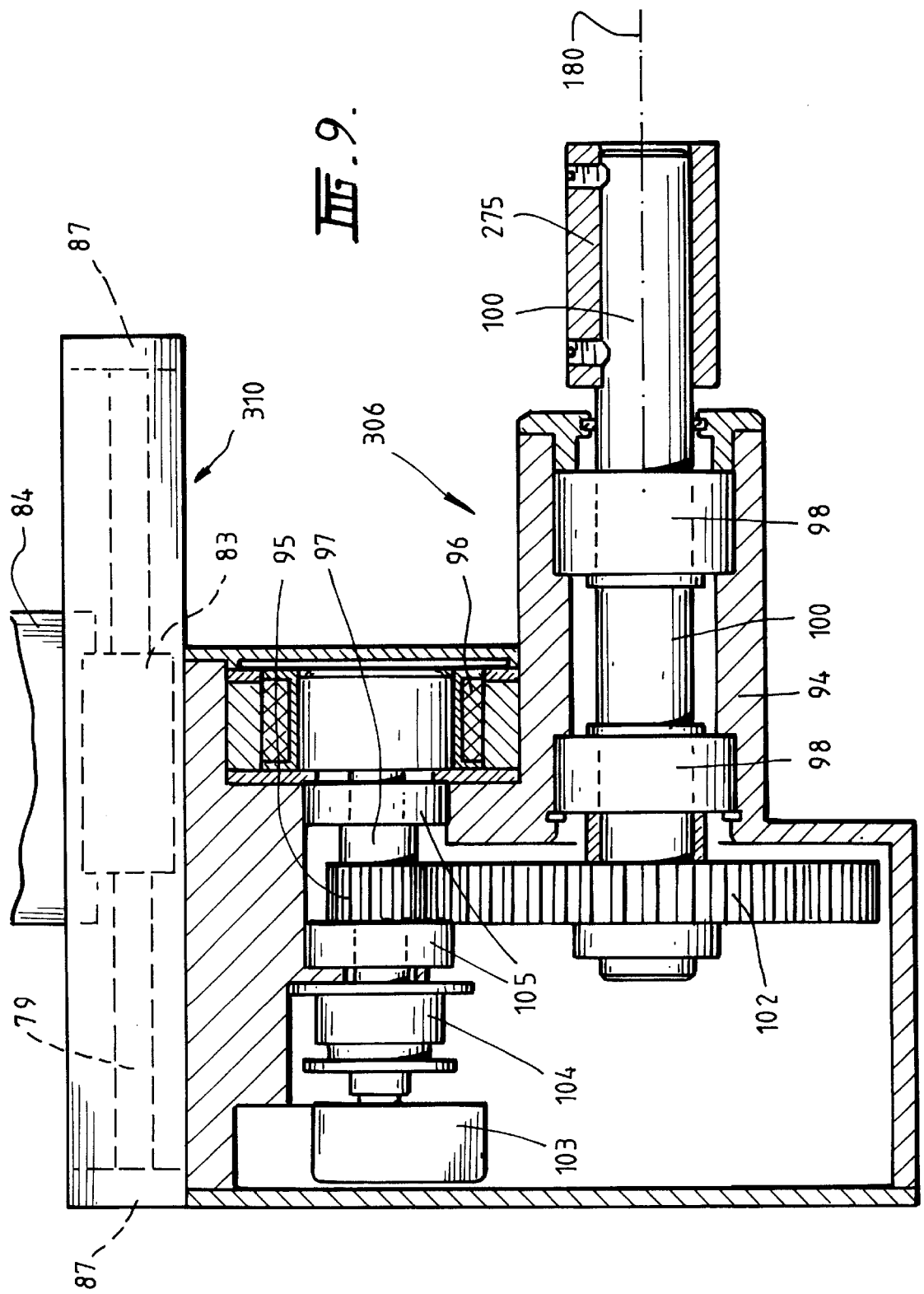
FIG. 9 illustrates one form of ring rotation sub-assembly of the articulated arm.
Figure 10:
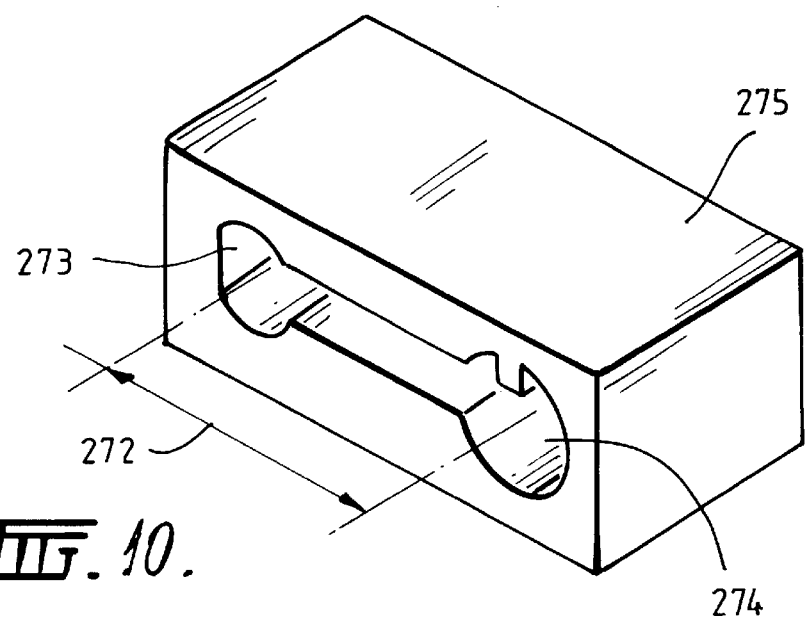
FIG. 10 illustrates one form of coupling that maybe employed with the articulated arm.

A preferred embodiment of a ring drive assembly will now be described with reference to FIG. 9. The ring drive consists of a motor 96, bearings 98 and 105, a housing 94, transmission shafts 97 and 100, a position sensor 103, a gear train 95 and 102, and a brake 104. The ring drive assembly carries the arch support 300, the arch 124 and hence the pivot length drive, via a coupling 275 (FIG. 10). The rotational movement provided by the ring drive is limited to ±180 degrees. As the ring drive rotates the arch drive assembly and pivot length drive assembly, it brings the tool to address different angular positions 181 with respect to the patient (FIG. 15). Wires 289 from the ring drive join a separate insulated and shielded conduit 290 and terminate at the lower portion of the column 84.

The arch drive axis 308 together with the pivot length drive axis, are arranged to be confined in a plane 285 (FIG. 1). This is to save space. When the ring drive operates, this plane rotates and forms an angle with a plane 284 that contains the head drive and ring drive axes. The planes are displaced by an offset 272 which can be alterable.

The offset 272 is alterable by means of the coupling 275 illustrated in FIG. 10. The extension 113 of arch support 300 is non-rotatably received in recess 274 of coupling 275, whilst the transmission shaft 100 of the ring drive assembly is non-rotatably received in the recess 273 of the coupling. Hence, rotation of shaft 100 will produce a pivoting movement of the coupling 275, which in turn produces an orbital motion of the arch support and its associated assemblies about the ring drive axis 180. The radius of orbit, corresponding to the offset 272 can be altered simply by replacing coupling 275 with another coupling of different length. Alternatively, an adjustable offset of variable length may be employed.

The length of the extension arm 113 of arch support 300 can be altered to accommodate different tool lengths. A telescopic arm can be used. The coupling void 274 can accommodate a limited difference in length, by sliding the arm in it. Also, 113 is made modular so that a different length of 113 can be selected. However, too long an arm will not be desirable as the bending movement about the ball joint 163 will be great. Although 163 can be modified dimensionally and/or texturally to suit the need, handling the articulated arm becomes prohibitively difficult.

Figure 11:
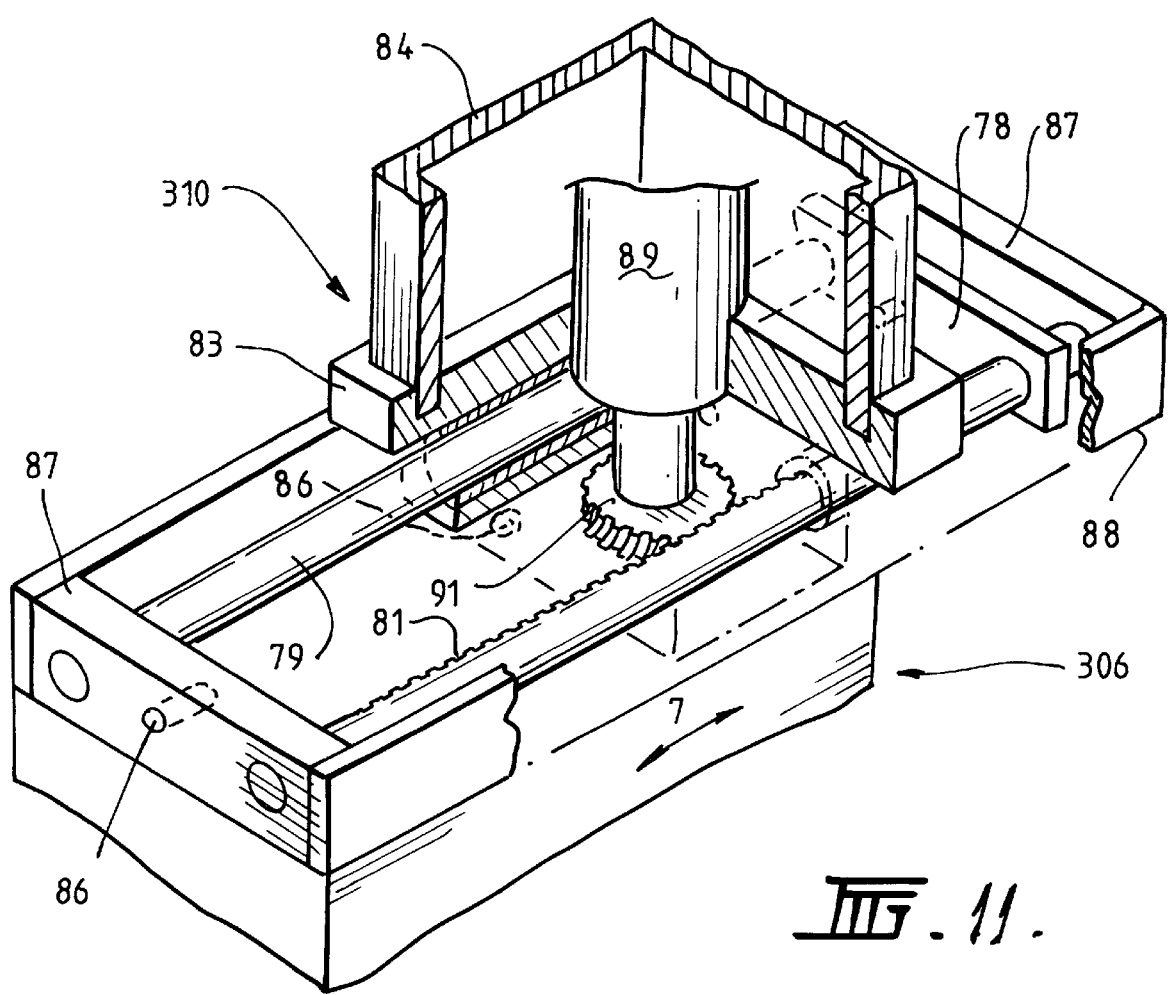
FIG. 11 illustrates one form of head travel sub-assembly of the articulated arm.

Finally, the head travel drive assembly 310, which is provided at the bottom of column 84, will be described with reference to FIG. 11. The head travel drive assembly consists of a motor 89, a position encoder (not shown), a rack 81 and pinion 91, a guide rail 79, endplates 87, housing 83, limit switches 86 and base plate 88 (FIG. 11). The head travel drive moves all the assemblies described in the preceding paragraphs in a horizontal fashion, sagitally 1 (FIG. 1) with respect to the patient. This allows different prostate lengths to be administered. All conduits and wires terminating at the column 84 are connected to four or five sockets 291 at the upper end of the column. Corresponding plugs affixed on the Y-arm of the counterbalance support system can be connected to these sockets to prepare the robot for use.

At the upper end of the column 84, a bolt with a spherical head 164 is secured firmly. The spherical head 164 is to engage into a ball joint assembly 312 designed to facilitate rapid connection/disconnection of the articulated arm to a counterbalance support system (see FIG. 13). The head travel has a movable limit stops 78 that positively (by way of jam bolts 85 and limit switches 80) prevents the tool, being carried by the arm, from going beyond a safe limit, even when there is a discrepancy in the software driving the head travel motor.

Advantageously, the pivot length drive is self-contained and can be detached for a stand alone application. It is therefore capable of being held by a mechanised holder such as, but not limited to, an Elmed retractor to perform such useful tasks as urodynamics study where the diagnostic probe, usually ultrasound, has to be moved at fixed and accurate intervals. These linear movements can be delivered by the pivot length drive alone. The same argument extends to other axes of the articulated arm, either individually or in combination, as they are modular by design.

In a preferred embodiment of the current invention, the articulated arm is suspended on a counterbalance support system (FIG. 13) via a ball joint 164 (FIG. 1) which is manually lockable by means of a handle 168. The counterbalance support system provides three degrees of linear freedom, 8 (X), 7 (Y) and 6 (Z), plus a rotational swing 5 (R). The latter allows a quick swing away of the robot when human intervention is necessary in an emergency.

The Z movement 6 is counterbalanced by a suitable number of deadweights 248 hidden in the main column 28. (see FIG. 12). The counterbalance support system includes a horizontal Y-arm 17, a horizontal X-arm 18 from which the articulated arm is suspended, and a vertical main column 28. When appropriately tuned, the total weight of the Y-arm 17, X-arm 18 and the articulated arm (FIG. 2) is balanced. Hence, very little effort is required by the human operator in order to move the assemblies during a setup procedure.

The X, Y and Z movements of the counterbalance support system provide continuous movement along the respective axes. The physical arrangement is such that the X arm 18 is carried by the Y arm 17 which is in turn carried by a column rotation assembly, which in turn is carried by the Z arm (on the main column 28) via a swing bracket assembly 19 (see FIG. 13). The load being carried rides on a bearing guide 30*a* and 30*b* (FIG. 12), 240*a* and 240*b* (FIG. 14) which is able to withstand the bending moment and torsional torques. In the swing bracket assembly 19, the Y arm 17 rotates on a sliding bearing about a swivel shaft 29, (FIG. 13). Unlike the linear axes, the rotational axis has intermittent steps of rotation. A plunger 36 is spring loaded and falls into a series of tapered holes 39 to give very positive locking action. To unlock, either a solenoid 35 is activated, or the plunger button 32 is compressed, both lift the plunger off its seat, thus allowing swivel action of the horizontal Y-arm 17. (FIG. 13).

Within each of the X arm 17, Y arm 18 and main column 28 means for slidably moving the articulated arm in the X, Y and Z directions respectively are provided. FIG. 14 provides a cut away view of the X arm 18 illustrating a preferred means of effecting the sliding movement. A cable and pulley system is used comprising an endless cable loop 239 received on guide pulleys 237 provided at both ends of the arm. A bearing mounted slide unit 240*b* is slidably mounted on a linear guide 240*a* and is provided with a ball joint attachment 241 to which the ball joint assembly 312 is connected. The slide unit 240*b* is fixed to the cable 239, and its sliding movement on the linear guide 240*a* is limited by rubber stoppers 243. Along the cable path, one or two locking mechanisms can be installed, depending on the stroke length. As a fail safe feature, the cable, and hence the load being carried, is normally prevented from moving. This is accomplished by a clamping lever 268, pivot pin 266 and spring 269, the cable 239 is gripped by the lever under the spring force acting at a pivot distance 265. To unlock the cable, the solenoid 236 (FIG. 14) can be activated electrically, which pulls the lever away from the cable, thus freeing it. A manual override lever 34 is provided to allow manual override, in case of power failure or unforeseeable circumstances. The cable and pulley arrangement is repeated in all the linear axes, with slight alterations, particularly stroke length. (see FIG. 12, solenoid 249 and manual lever 247).

In the illustrated embodiment of the current invention, the counterbalance support system is in the form of a trolley system that can be wheeled around for transportation or storage purpose. The trolley is equipped with shelves 25, 26 and 27 (FIG. 13) for the housing of personal computer systems, surgical instruments and a motion control system. The trolley has a base 24 that can be lowered such that the entire system, including the robot, rests on the floor on four footings. The weight of the system ensures that, even with the apparent overhang of the Y-arm the system is sufficiently rigid and stable with respect to the patient throughout an operation or operations. When the operation is complete or not required, the robot and its trolley (counterbalance support) system can be wheeled away. This is achieved by applying a force on a foot pedal 254 to lift up the base and have the wheels 257 engage with the floor and bear the weight of the overall system.

In a setup procedure for TURP, the target to be established as the reference position of the robot is the verumontanum, which is the junction of the ejaculatory duct and the prostatic urethra. The verumontanum is identified under direct endoscopic vision. When it is found, the endoscope/cystoscope/resectoscope is fixed in space by an appropriate holder such as a Greenberg retractor or an Elmed retractor. It should be appreciated that the orientation of the endoscope is arbitrary when the verumontanum is found. When the endoscope is fixed, the articulated arm is then brought into engagement with the endoscope.

Moving the orientation and position of the articulated arm, relative to the patient who is fixed under his own weight or with some suitable method of strapping (see FIG. 2), is facilitated by the counterbalance support system, mainly by its three linear axes which must first be unlocked by activating the corresponding solenoids, such as solenoids 236, 249 and the ball joint. In the first approach, the surgeon manipulates the articulated arm, lifting it or lowering it, shifting it sideways, swivelling it about the ball joint, until the C-bracket 151 enters into the grooves 138 cut on the carriage 137 of the articulated arm, (see FIG. 3). Alternatively, to avoid the use of a passive holder, the articulated arm and the tool holder are brought close to the endoscope, which is then engaged onto the carriage 137, disturbing it slightly from the reference position; followed by moving the articulated arm together with the endoscope (as one body without moving the robot's axes) to re-establish the verumontanum location. These two approaches are both valid, their use depending on the surgeon's preference and skill.

The counterbalance gantry can be provided with a plurality of cameras at the same level as the X-arm 18. This is to enhance the safety of the articulated arm during an operation. The cameras are to observe markers or stripes strategically placed on to the robot and are properly calibrated so as to obtain optimal accuracy. Knowing directly the joints rotation or translation using machine vision, and with known kinematics and geometry of the arm, the tip of the cutter can be ensured to always move within a predefined safe working envelope. Any movement outside this envelope will trigger a suspension of motion and an alarm to warn the user.

The C-bracket 151 is previously fastened onto the resectoscope/endoscope and sterilised together with it. Securing of the C-bracket 151, hence the resectoscope, is achieved by turning the two levers 150, preventing it from dropping out of the grooves 138 of the carriage 137. The X, Y, Z and R axes of the counterbalance support system are then locked by de-activation of their respective solenoids 236, 249 and 35. This is a fail safe feature in that the axes are normally locked when the solenoids are not powered. The retractor is then removed by unlocking the lever 156 and sliding the pin 154 away from the C-bracket. The setup procedure is then complete. Although the verumontanum has been used in the above paragraphs to show a setup procedure for TURP, it should be appreciated that other targets, to be identified endoscopically and referenced, or other kinds of intervention, can benefit from the same setup procedure.

Figure 17:
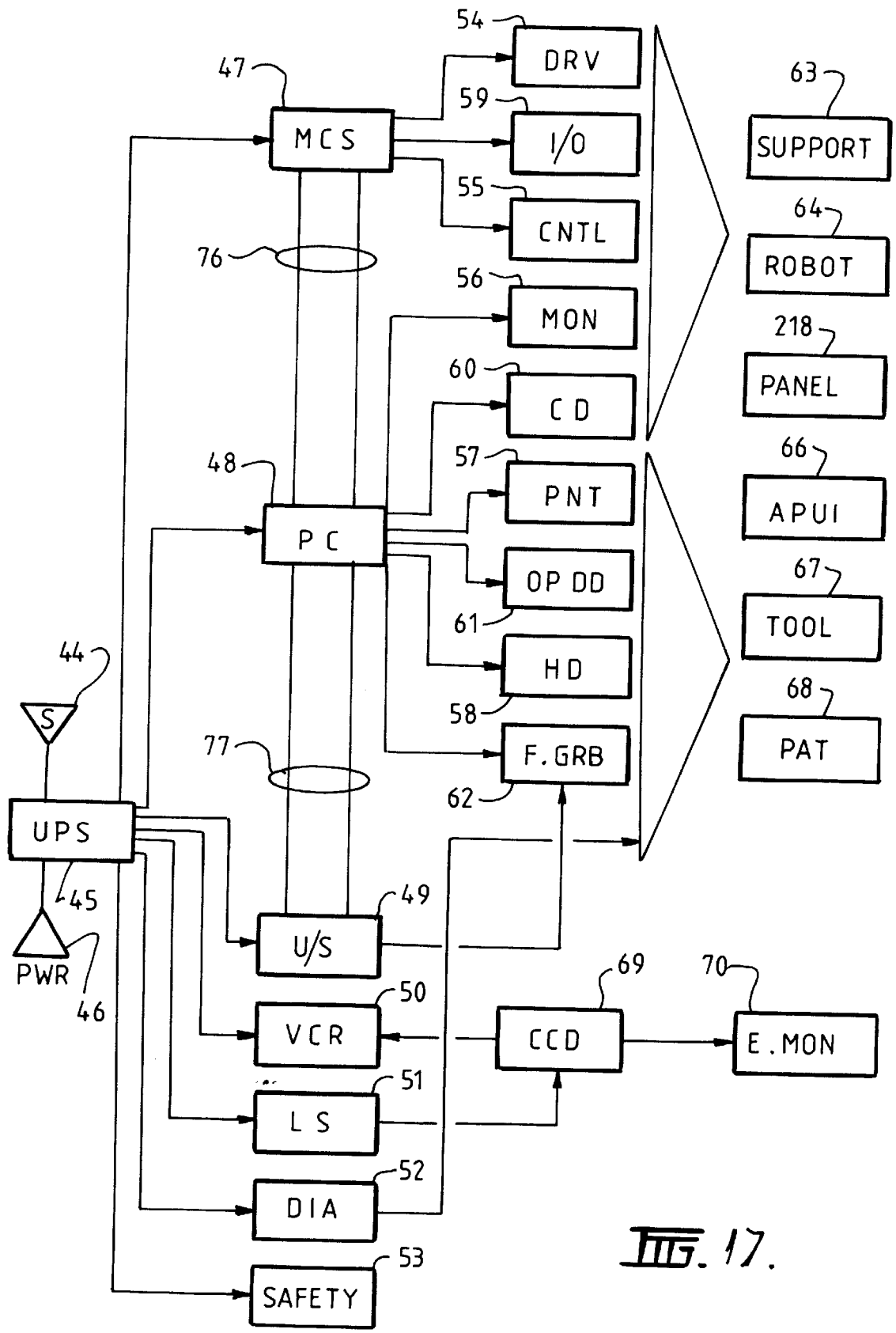

The articulated arm, like other known robot systems, may be controlled by a motion controller 47 which in turn is supervised by a portable personal computer 48, via RS232 communication 76 (see FIG. 17). Motorisation 73 of the respective axes (positioning, velocity, acceleration, and coordination) are controlled using a conventional PID control loop implemented digitally on a state of the art microprocessor based multi-axis motion control system 47. Position sensors, such as, but not limited to, a differential optical encoder 71, can be employed to provide both positional and velocity-information for the control loop. The motion control system is also capable of a number of signal input and output functions 59. These so called I/O functions are normally used to capture the status of limit switches, 74 and 75, for the purpose of "homing", turn on or off equipment working in conjunction with the robot send off alarm or light indication to serve as a warning of danger or other important events etc. The above mentioned motion control system is well known and is widely available commercially and will not, therefore, be described in detail here.

Barrel cavity generation, as shown in FIG. 15, is a typical form of resection capable of being performed by the articulated arm design. In this cutting strategy, one or more axes of movement are involved at any one time. Coordinated movement of the arch and pivot length drive to trace a, so called, sagittal line 185 being the ideal. Computer reconstruction of ultrasound images facilitates the determination of a series of sagittal lines in a round the clock fashion 181. The ring axis brings the resectoscope to address each of these sagittal lines. In the case of electrocauterisation, tracing, and hence cutting, along the sagittal line is repeated clockwise and counter-clockwise and progressively outwards till the surgical capsule 279 (FIG. 15) is reached. In the case visual laser TURP (such as VLAP, visual laser ablation of the Prostate), the speed of withdrawal of the laser fibre and its spatial power pattern can be controlled on the fly (i.e. dynamically) so as to achieve optimal cutting, not quite possible by a human operator. Similar argument extends to TUNA (transurethral needle ablation of the Prostate) where the needles are to protrude/retract at different clock positions to different depths and the power setting is to be controlled in a manner quite cumbersome for a human operator.

FIG. 17 is a circuit block diagram showing typical components which the linked arm can work in conjunction with to carry out useful and safe activities. These components are:

An uninterruptable power supply 45 to supply power to the system continually. It sustains the system to operate for at least 10 minutes (depending on the capacity of standby battery 44) in the event of a power failure.

A 4-axis motion controller 47 with input-output functions 59, that can be interrupt driven. The motion controller can be stand alone or mounted on an expansion slot in a personal computer 48. Communication with the PC in the stand alone case is via a RS232 line, while the latter is via a local bus.

A personal computer 48 with a usual display monitor 56, hard disk 58, floppy disk drive, RAM and ROM operating memories, operating system, printer 57, and optional external storage devices such as a compact disk drive 60, and an optical disk drive 61.

A diagnostic ultrasound scanning system 49. Either transrectal or transurethral probe or both can be used. A frame grabber 62, installed on the PC 48, captures the ultrasound images from the ultrasound scanner via a set of co-axial video signal cables. Communication between the ultrasound scanner and the computer is optional, but can be established using the GPIB standard conformed to IEEE 488,77.

A video cassette recorder 50, to archive ultrasound and/or endoscopic images, intra, pre- or postoperatively.

A remote light source 51, supplying cool light via optical fibres to the operating site and the scene captured by CCD (charged coupled device) camera 69, for maximum efficiency. The image, in the form of electronic signals, can be processed and enhanced and finally displayed onto an endoscopic monitor screen 70.

Energy source 52 for cutting. In the case of electrosurgery, this is the so called diathermy unit. In the case of laser surgery, this will be a generator for high intensity laser light source.

A hard logic safety monitor 53, contains programmable logic arrays that will monitor logic status of critical parameters and send out interrupting signals to suspend the robot action, or warning signals to alert the user of any untoward events during an operation.

Figure 16:
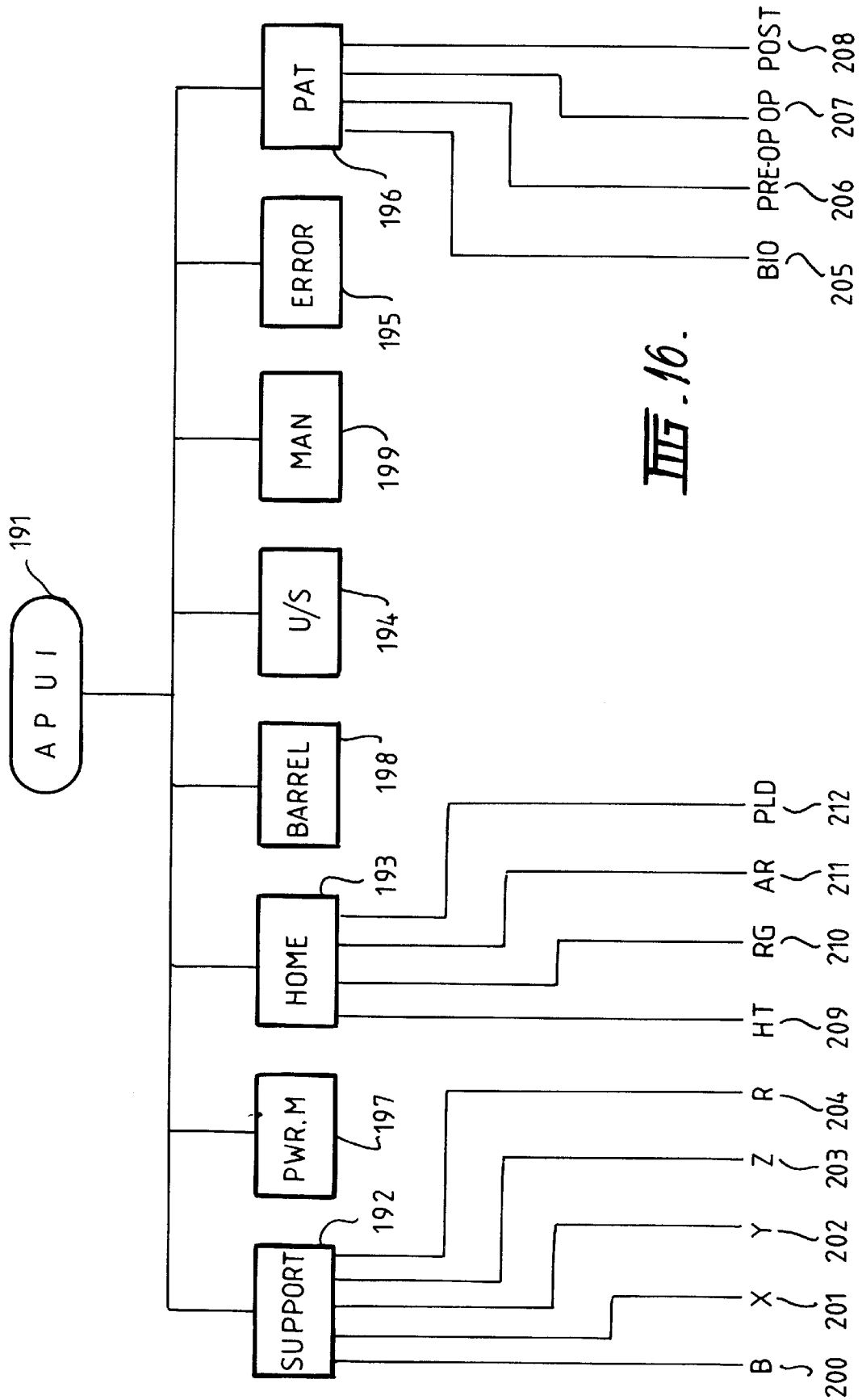
FIG. 16 shows the modular structure of the surgeon interface software, which is designed to allow self-guided event driven operation of the articulated arm; and, FIG. 17 is a functional block diagram of the overall system, showing components of the system, their inter-relations and control.

The personal computer executes an interface software 191, called APUI (Automated Prostatectomy User Interface), which carries out tasks as outlined in FIG. 16. Each task to be performed by the user interface is designed to occupy a page of screen display, with pop-up windows and pull down menus to offer versatile selections.

Support 192, displays a screen with control buttons and status boxes to control the activation (or deactivation) of locks of the counterbalance support system, in combination or individually. It also displays the lock status of each of the axes of the counterbalance support system, (except B, 200) X, 201, Y, 202, A, 203, R, 204, which correspond to the axes of the counterbalance support system (FIG. 13), 8, 7, 5 and 6 respectively.

A homing sequence of the robot, after or before the setup procedure is accomplished, is carried out by a subroutine in the interface called HOME, 193. This routine brings each of the axes of the robot to a suitable reference position influenced by the size and orientation of the target that is to be addressed by the robot. HOME occupies a screen display page, again with pop-up windows and pull down menus to facilitate selection of a large variety, including redefinition of home position of the axes.

A frame grabber board F.GRB 62 and biaxial cable take and transfer images respectively from the ultrasound scanner. A state-of-the-art software for image processing, together with customised software routines, process the images. The end results are used to guide the operation to be performed by the articulated arm.

The desired movement, or combination of movements, to achieve the intended work envelope within the patient, and events like switching, adjusting the power setting, etc., are formulated into commands understood by the motion controller and sent to it by the personal computer via RS232 (or serial) lines 76. The software routines that handle this translation are grouped under BARREL 198.

The articulated arm is also capable of manual control where joysticks, foot or finger switches, at appropriate locations, are provided for flexible control of the movements of the robot manually. To interpret the controls from joysticks and the like, routines in MAN 199 undertake the translation.

Patients' biodata are captured using PAT 196, of the APUI. These data can be the amount of tissue removed, time taken, age of patient, etc., which are of interest to researchers. Statistical tools, either standard or customised, can be integrated with PAT 196.

Power supply to the robot system is monitored by PWR.M 197, of the APUI. It performs the necessary actions to ensure continuous operation of the robot system without degradation, in the event of a power failure. Graceful degradation of the system will be initiated after a predefined period of time.

ERROR handling routines 195 are to handle both foreseeable (normal error handling—for example, memory overflow, loss of communication etc.) and unexpected (exception handling) errors. Recovery procedures will be activated for the first type of errors to restore system operation. Attempts to recover will be activated for unexpected errors, but will generally lead to a graceful shutdown. In addition, 195 also comprises safety monitoring routines. For example, when the tool holder axis is not moving, cutting power will not be allowed to switch on.

In order to place the work envelope of the cutting tool, or other forms of implement carried by the robot, in a desired location within the patient, and to know the limit of is the work envelope, it is desirable that some form of image guidance be used for the articulated arm. Ultrasound imaging, both transrectal and transurethral, have been found adequate and safe for such a task. To avoid the problem of patient registration, that is the matching of pre- and intra- (sometimes even post-) operative data, it is best that the imaging process shares the same reference frame as the robot system. This means the imaging process has to be done intraoperatively with some form of adaptor for the imaging probe and the cutting tool (or other implements). Being intraoperative, dimensional and locational measurements of the target have to be accomplished quickly so that the process does not add significantly to the overall operating time. This can be achieved by using computer image processing techniques.

Figure 5:
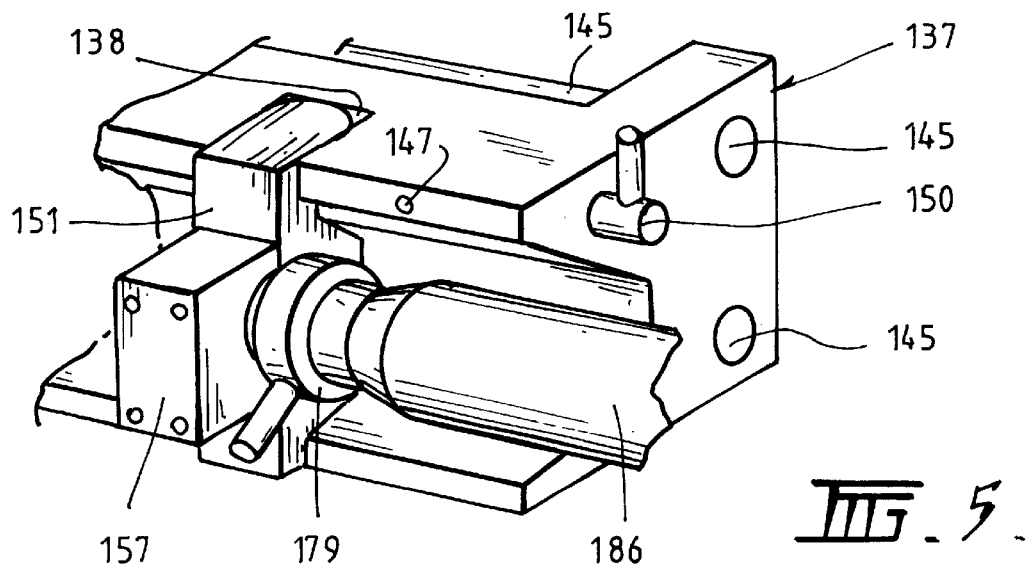
FIG. 5 illustrates how a transurethral ultrasound probe can be mounted onto the tool holder of the pivot length drive assembly.

To facilitate the above method, it is a preferred aspect of the current invention that provision is allowed for both transrectal and transurethral intraoperative scanning of the target to be treated. Transurethral scanning is possible by leaving the outer sheath of the endoscope, which is attached to the carriage (or tool holder) of the articulated arm, in the patient. In the place of the usual working element is the transurethral ultrasound probe 186 (see FIG. 5). During scanning, only the head travel is moved, bringing the probe in and out of the patient to obtain the needed transverse scan data. The probe is replaced by the working element when the scanning is completed, thus sharing of the same frame of reference is realised. The arch stays put at its zero degree, or horizontal, position throughout the scanning process.

Figure 6:
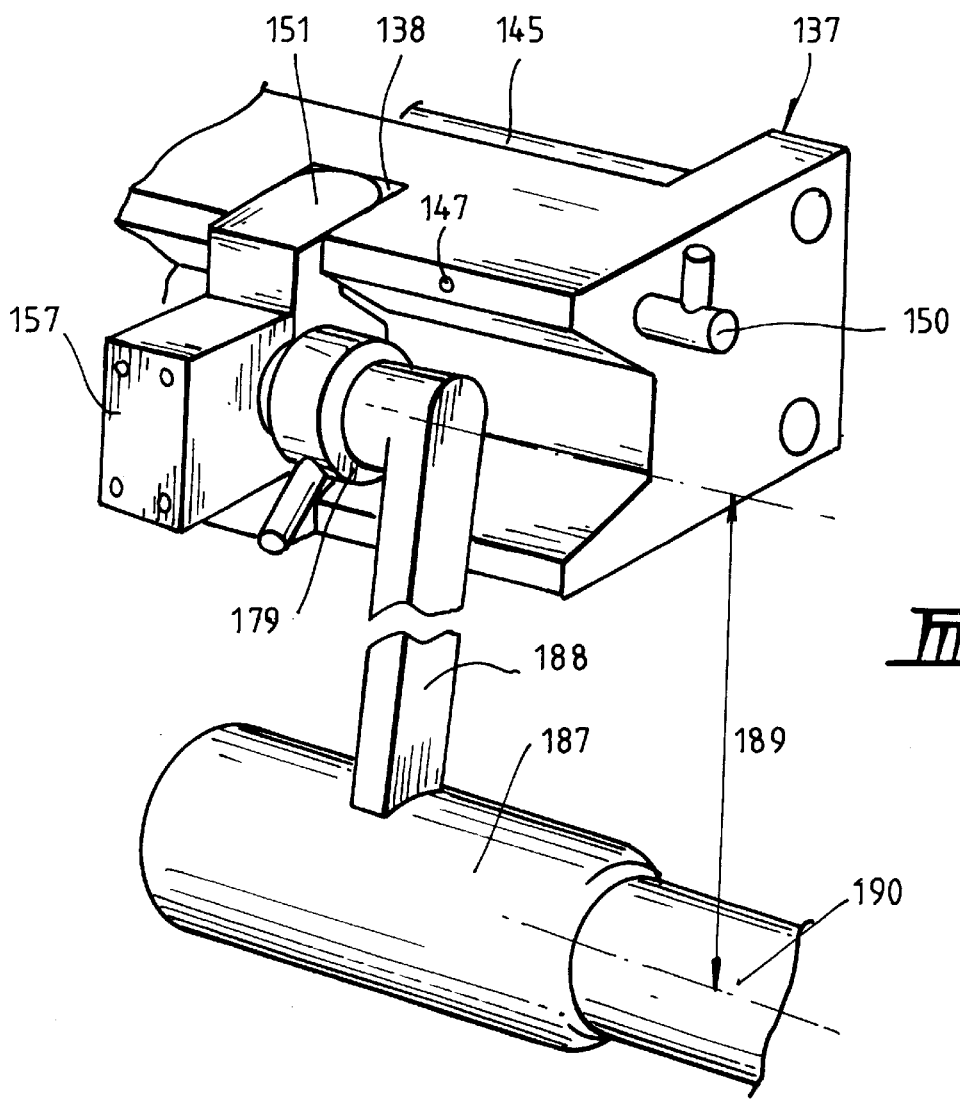
FIG. 6 illustrates how a transrectal ultrasound probe can be mounted onto the tool holder of the pivot length drive assembly.

Transrectal scanning is possible by way of an attachment (see FIG. 6), which has an extension 188 with one end adapted to the outer sheath of the endoscope and the other a holder 187 for the probe body 190. The extension is adjustable so that the entrance, governed by the offset 189, to the rectum is fairly level. Grabbing of the probe body is variable along its length to accommodate different setup conditions and patients. As in the case of transurethral scanning, only the head travel is moved, and the probe and extension are replaced by the working element when scanning is complete.

In a TURP, or procedure to address BPH, the information to be obtained in an ultrasound scanning is the coordinates of the boundary known as a surgical capsule. Cutting beyond the surgical capsule is not desirable as it can lead to incontinence, impotence or torrential bleeding. The first two complications are due to nerve endings, a fair amount of which lie just behind the capsule, being damaged as a result of cutting. The reason for torrential bleeding is obvious—big vessels are usually situated outside the capsule.

It is not immediately obvious in a transverse ultrasound scan where the capsule boundary is. It requires a trained eye to pick it up and very often not completely and precisely. The articulated arm can perform an intraoperative ultrasound scanning either semi-automatically or automatically. Routines in 194 cater for this purpose. In semi-auto scanning, the surgeon has to outline the boundary using a digitizer such as a mouse. In auto scanning, the image analysis algorithms will do the job (of course to be approved by the surgeon when done). The choice of which mode of scanning to use is a matter of convenience versus safety. Both must not add significantly to the operating time.

Preferably all the drive assemblies can be draped in a sterilised bag just prior to an operation. The bag can be conveniently fastened onto the column structure 84 of the head drive assembly. It has ample sag room to allow movements of the articulated arm during an operation yet preserving sterility. The entire system is best arranged in a manner shown in FIG. 2 where the robot is shown suspended on the counterbalance support structure which, with its trolley platforms 25, 26 and 27, also houses the computing and surgical equipment. Endoscopic view is shown on a monitor 259 suitably supported 21 to give comfortable viewing.

Figure 2:
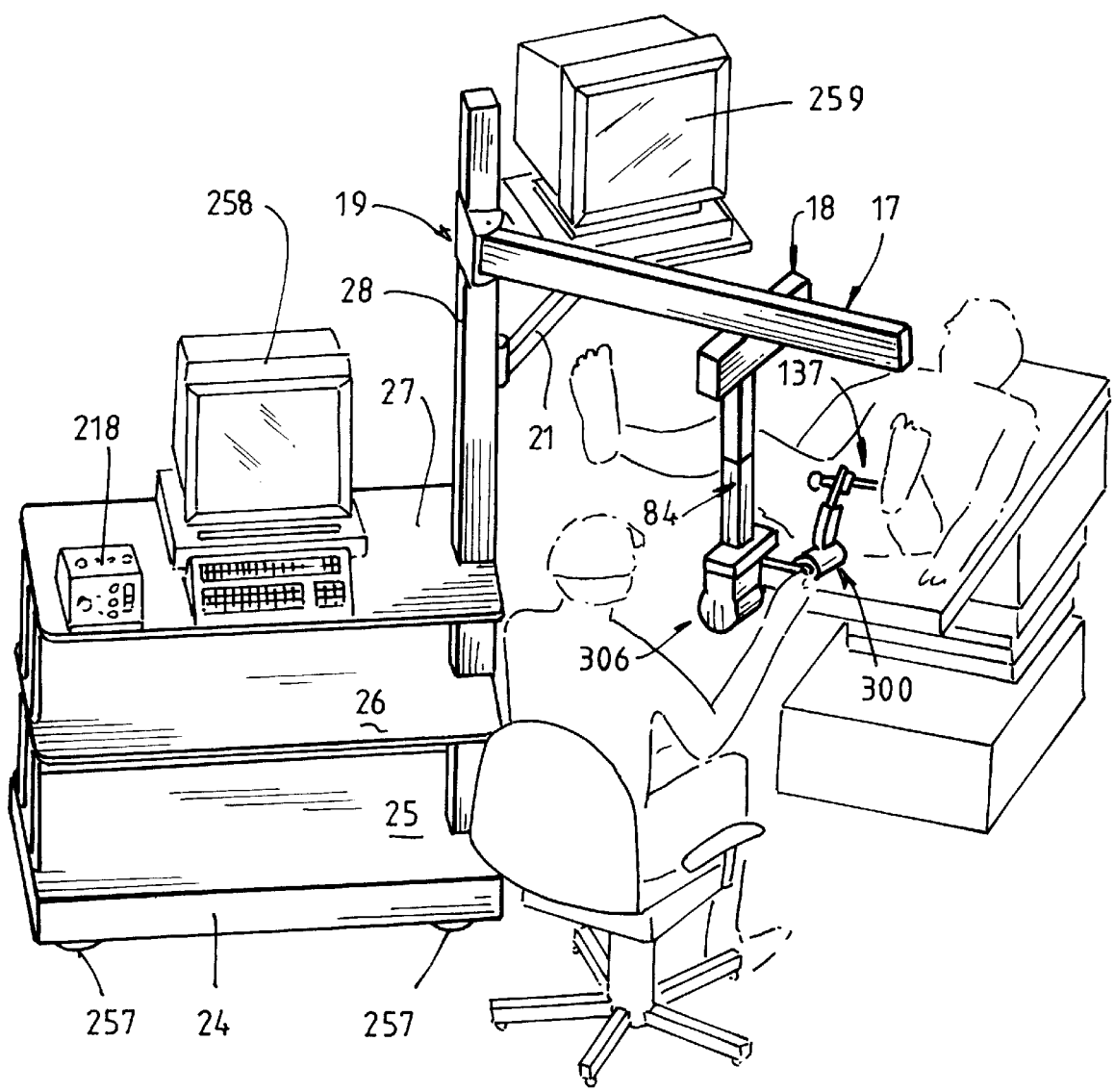
FIG. 2 is an isometric view of the articulated arm and counterbalance support system as it would be used in an operating room to perform TURP.

To ensure maximum safety and convenience of operation of the system a control panel 218 is placed next to the computer console 258 on the trolley platform (see FIG. 2). There are visual indicators on the control panel to display operating status of each axis of the motion controller. When activated, an emergency switch cuts off power supply to the motors and cutting power sources only, leaving all other system components still functional. Even so, this is a more drastic measure compared to the keyboard interrupt feature installed in the user interface routine. The keyboard interrupt feature is enabled once any, or a number of motors, is set into motion. By hitting any key on the computer keyboard, all motor movements can be killed or suspended.

Although it has been shown that an excellent target for the articulated arm is the prostate gland, it should be appreciated that it can also be used for other targets, for example, the bladder, the womb, etc. Furthermore, the treatment modality is not limited to electrocauterisation, but may include other modalities such as laser, high intensity ultrasound, TUNA (Trans Urethral Needle Ablation), etc. The articulated arm is designed so as to be capable of holding a wide range of medical tools and to facilitate more precise and accurate medical interventions in an operating theatre. With the help of computerised motion control, the system is able to carry the tools, one at a time and to conduct useful medical interventions. In so doing, it assists the surgeon to perform his/her task better in terms of time consumption, skill, accuracy and hence safety. These may lead to additional benefits such as low mortality, low morbidity, fewer assistants and nursing staff, less consumables, and lower risks by avoiding prolonged operating time.

The arm is typically made such that the drive assemblies are modular. This allows an entirely different kinematic configuration to be obtained by replacing the existing drive and support members with new ones. Wires are self contained in a drive and connectors are provided to enable control and drive signals to reach and leave the drive.

Now that a preferred embodiment of the articulated arm has been described in detail, numerous variations and modifications will suggest themselves to persons skilled in the relevant arts, in addition to those already described, without departing from the basic inventive concepts. All such variations and modifications are to be considered within the scope of the present invention, the nature of which is to be determined from the foregoing description and the appended claims.

It is claimed:

1. An articulated arm for performing medical procedures with a medical tool, the arm comprising:

an arcuate member slidably mounted on a first movable support member;

a tool holder for holding the medical tool in an operational position, said tool holder being carried by the arcuate member; and, a first drive assembly provided on said first support member for slidably moving said arcuate member with said tool holder, wherein said tool holder can be moved along an arcuate path so as to alter the operational position of the tool in a predetermined manner, and wherein said arcuate member is removably mounted on said first support member, and wherein another arcuate member having a different radius of curvature can be slidably mounted on the first support member.

2. An articulated arm as defined in claim 1, further comprising a second drive assembly provided in connection with said tool holder for moving said tool holder along a linear path, said linear path intersecting an axis passing through the centre of curvature of said arcuate path.

3. An articulated arm as defined in claim 1, wherein said tool holder comprises a slidable carriage provided with a pair of grooves adapted to receive a removable tool mounting bracket therein, each groove having an associated locking lever for locking the tool mounting bracket to the carriage, said locking levers having a flat provided along a longitudinal edge thereof whereby each of the locking levers can be rotated to a position where the flat is flush with the respective groove to facilitate insertion or removal of the tool mounting bracket.

4. An articulated arm as defined in claim 3, wherein said pair of grooves are one of a plurality of pairs of grooves provided in the carriage to allow the location of tool mounting bracket to be varied to vary the operational position of the medical tool.

5. An articulated arm as defined in claim 3, wherein said tool mounting bracket is in the form of a C-bracket forming one half of a bracket assembly, the other half of the bracket assembly being in the form of a clamping bracket adapted to clamp the C-bracket to a body of a medical tool.

6. An articulated arm as defined in claim 3, wherein said carriage is slidably mounted on a pair of guide rails and is provided with a rack and pinion arrangement for sliding movement of the carriage along said guide rails, the tool holder further comprising a motor for driving the rack and pinion arrangement to effect said sliding movement of the carriage.

7. An articulated arm as defined in claim 1, wherein said first support member is provided with first and second stiffening members between which said arcuate member is slidably supported.

8. An articulated arm as defined in claim 7, wherein said arcuate member is provided with an external gear profile and said first drive assembly includes a motor that engages with said external gear profile to slidably move the arcuate member along said arcuate path.

9. An articulated arm as defined in claim 2, further comprising a third drive assembly mechanically coupled to said first support member for pivoting said first support member about a first drive axis, whereby said tool holder carried by the arcuate member can also be pivoted about said first drive axis.

10. An articulated arm as defined in claim 9, wherein said first support member is coupled to said third drive assembly by means of a coupling adapted to produce an offset between said first drive axis and a longitudinal axis of said first support member whereby, in use, a central axis of the medical tool held in the tool holder intersects said first drive axis so as to define a pivot point of the tool.

11. An articulated arm as defined in claim 10, wherein said coupling is a removable coupling which can be replaced with a different coupling to produce a different offset so as to accommodate a different medical tool.

12. An articulated arm as defined in claim 9, further comprising a second support member for supporting said third drive assembly, said second support member being provided with a fourth drive assembly for moving said third drive assembly in a linear direction whereby, in use, said tool holder together with the arcuate member can also be moved in said linear direction.

13. An articulated arm as defined in claim 12, wherein each of said first, second, third and fourth drive assemblies include an electric drive motor and wherein each of said drive assemblies are under the control of a microprocessor based multi-axis motion control system.

14. An articulated arm as defined in claim 12, wherein said second support member is suspended on a counterbalance support system providing at least four degrees of freedom of movement.

15. An articulated arm as defined in claim 14, wherein said counterbalance support system is provided with first and second mutually perpendicular support arms allowing X and Y axis movement respectively of the articulated arm, and a vertical support column allowing Z axis movement of the articulated arm.

16. An articulated arm as defined in claim 15, wherein said articulated arm is slidably mounted on said first support arm by means of said second support member, said first support arm is slidably mounted on said second support arm, and said second support arm is slidably mounted on said support column, and wherein each of said first and second support arms and said second support member can be locked in position by respective first, second and third locking means.

17. An articulated arm as defined in claim 16, wherein sliding movement of each support arm of the counterbalance support system is effected by a cable and pulley system, and wherein said locking means comprises a cable clamp.

18. An articulated arm as defined in claim 15, wherein said slidable mounting of the second support arm is provided with a swing bracket assembly to enable the second support arm to pivot horizontally about its slidable mounting on the support column.

19. An articulated arm as defined in claim 18, wherein said counterbalance support system further comprises a trolley forming a base on which the vertical support column is mounted, and having a plurality of shelves provided thereon for supporting other equipment.

* * * * *